United States Patent [19]
Ehrhardt et al.

[11] Patent Number: 5,929,230
[45] Date of Patent: Jul. 27, 1999

[54] ACYLATED SUCROSEMONOCARBOXYLIC ACIDS

[75] Inventors: Sonja Ehrhardt, Gross-Gerau; Markwart Kunz, Worms; Mohammad Munir, Kindenheim, all of Germany

[73] Assignee: Südzucker Aktiengesellschaft, Mannheim, Germany

[21] Appl. No.: 08/747,355

[22] Filed: Nov. 13, 1996

[30] Foreign Application Priority Data

Nov. 14, 1995 [DE] Germany .......................... 195 42 303

[51] Int. Cl.$^6$ ................. C07K 5/00; C11D 1/00

[52] U.S. Cl. .............. 536/123.13; 536/115; 536/119; 536/122; 252/174.18

[58] Field of Search .................... 536/115, 119, 536/122, 123.13; 252/174.18

[56] References Cited

U.S. PATENT DOCUMENTS

| | | | |
|---|---|---|---|
| 3,714,144 | 1/1973 | Feuge et al. | 260/234 R |
| 3,872,020 | 3/1975 | Yamagishi et al. | 252/89 |
| 5,270,460 | 12/1993 | Dordick et al. | 536/115 |

FOREIGN PATENT DOCUMENTS

| | | |
|---|---|---|
| 1467705 | 11/1969 | Germany . |
| 2022880 | 7/1971 | Germany . |
| 41 31 505 | 3/1993 | Germany . |
| 43 07 388 | 9/1994 | Germany . |
| WO80/00452 | 3/1980 | WIPO . |

*Primary Examiner*—Elli Peselev
*Attorney, Agent, or Firm*—Finnegan, Henderson, Farabow, Garrett & Dunner, L.L.P.

[57] ABSTRACT

The invention relates to acylated sucrosemonocarboxylic acids, the preparation and use thereof as surface-active substance.

18 Claims, No Drawings

ACYLATED SUCROSEMONOCARBOXYLIC ACIDS

DESCRIPTION

The invention relates to derivatives of sucrosemonocarboxylic acids, the preparation and use thereof as surface-active substances.

Sucrose esters are widely used, because of their amphiphilic nature, as industrial auxiliaries and additives. Thus, sucrose acetates are employed in the detergents sector as bleach activators and sucrose fatty acid esters are employed as surface-active compounds. On the industrial scale, these esters are mainly synthesized by a number of different transesterification processes. In the solvent process, sucrose is reacted with fatty acid methyl esters in the presence of a basic catalyst in a solvent such as dimethylformamide or dimethyl sulfoxide (JP 04,247,095). In the microemulsion process, the fatty acid ester is dispersed in a solution of the carbohydrate with the aid of an emulsifier. The solvent is removed before the reaction takes place (EP 0 254 376). In the solvent-free process, the so-called direct process, the fatty acid methyl ester is reacted with sucrose and a basic catalyst in the melt (GB 1 399 053). In other processes, lipases (DE 34 30 944) are used. Finally, it is known to carry out the esterification of sucrose with carbonyl chlorides and carboxylic anhydrides.

The known transesterification processes are very elaborate with regard both to carrying them out and to isolating the product. The reaction parameters of pressure and temperature must often be varied, and several extractions and distillations are necessary to isolate the sucrose eaters. In addition, the high reaction temperatures in combination with the long reaction times may lead to unwanted discoloration of the products. Although the sucrose carboxylic esters obtained in this elaborate manner show, as mono- and diesters, surface-active properties, they can be used as surfactants to only a restricted extent because of their limited solubility in water. The monoesters dissolve poorly in cold water, while the diesters can only be emulsified in water.

Specific preparation of the three possible sucrosemonocarboxylic acids has become possible only recently (DE 43 07 388). Derivatives of the sucrosemonocarboxylic acids have not to date, with the exception of the acetates, been described. The described derivatives of other carbohydrate acids are also predominantly acetates, which are frequently required as synthetic intermediates. It is common to most of these acylated carbohydrate acids that they have only very weak surface-active properties. For others, nothing is known about this.

The technical problem on which the invention is based is thus to provide sucrose derivatives which overcome the abovementioned disadvantages, that is to say are particularly suitable as surfactants and emulsifiers and can be prepared easily.

This technical problem is solved by providing acylated sucrosemonocarboxylic acids of the formula I

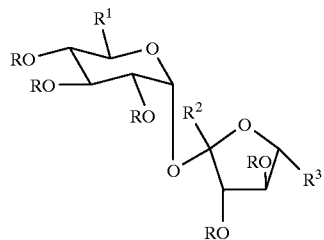

in which $R^1$, $R^2$, or $R^3$ is $CH_2OH$ or $COOH$, and R is H or CO—R', where $R^1$ is $(CH_2)_n$—$CH_3$ with n=14–16, and also a process for the preparation thereof and the use thereof as surface-active substances. The present invention accordingly provides acylated sucrosemonocarboxylic acid of the formula I

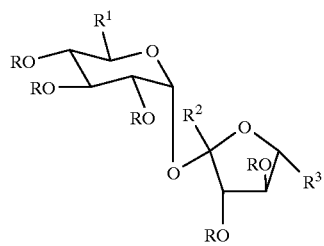

in which $R^1$, $R^2$ or $R^3$ is $CH_2OH$ or $COOH$, and R is H or CO—R', where R' is $(CH_2)_n$—$CH_3$ with n=4–16. The sucrose derivatives of the present invention are thus distinguished in that one radical out of $R^1$, $R^2$ or $R^3$ is COOH, while the other two radicals out of $R^1$, $R^2$ or $R^3$ are each $CH_2OH$, and at least one radical R is CO—R' with R' equal to $(CH_2)_n$—$CH_3$ with n=4–16. The present invention provides in particular 1-O-(β-D-fructofuranuronyl)-α-D-glucopyranosides ($C_6$-sucrosemonocarboxylic acid), 2-keto-6-O-(α-D-glucopyranosyl)-β-glucofuranonic acids ($C_1$-sucrosemonocarboxylic acid), 1-O-(β-D-fructofuranosyl)-α-D-glucopyranuronides ($C_{6'}$-sucrosemonocarboxylic acid), which are acylated with long-chain aliphatic carboxylic acids $C_6$ to $C_{18}$, or mixtures thereof.

These compounds have excellent surface-active properties and can therefore be used widely as industrial auxiliaries and additives, for example as surfactants, emulsifiers, stabilizers, softeners or solubilizers.

The sucrosemonocarboxylic acids or mixture thereof can be esterified using either a particular fatty acid or a mixture of several different long-chain aliphatic fatty acids $C_6$ to $C_{18}$. Accordingly, the sucrosemonocarboxylic acid acylated according to the invention may have different radicals R'. In a preferred embodiment, the invention relates in particular to an acylated sucrosemonocarboxylic acid in which —CO—R' is a caproic acid, caprylic acid, capric acid, lauric acid, myristic acid, palmitic acid or stearic acid residue.

The invention furthermore relates to aqueous solutions, soaps, cleaners such as scouring compositions or detergents (including shampoos, heavy duty detergents, bath additives), foodstuffs, cosmetics, emulsions, suspensions, jellies, creams, pastes, and powders, which comprise at least one of the acylated sucrosemonocarboxylic acids of the invention.

The invention relates in particular to a scouring composition which comprises 85% by weight to 95% by weight of quartz powder, 1% by weight to 5% by weight of alkalis (for example soda, borax), 1% by weight to 5% by weight of polyphosphates, 1% by weight to 5% by weight of the compounds according to the invention or mixtures thereof and 0% by weight to 1% by weight of active chlorine compounds. The invention also relates to a detergent, in particular a heavy duty detergent, which comprises 10% by weight to 25% by weight of the compounds according to the invention or mixtures thereof, 20% by weight to 60% by weight of complexing agents, 0% by weight to 30% by weight of bleaches, 0% by weight to 2% by weight of bleach activators, 0% by weight to 5% by weight of corrosion inhibitors, 0% by weight to 0.3% by weight of optical brighteners, 0% by weight to 2% by weight of antiredeposition agents, 0% by weight to 1% by weight of enzymes, 0% by weight to 0.2% by weight of perfumes and 0% by weight to 30% by weight of fillers. The invention also relates to cosmetics such as, for example, deodorant rollers which comprise 30% by weight to 60% by weight of alcohol, 0% by weight to 1% by weight of fragrances, 0.1% by weight to 1% by weight of deodorant agents, 0.5% by weight to 5% by weight of the compounds according to the invention or mixtures thereof and water.

The compounds according to the invention can be employed in various application forms, for example in the foodstuffs, pharmaceuticals, or hygiene sectors. The application form should moreover be adapted to the particular area of use.

The invention additionally relates to a process for the preparation of the acylated sucrosemonocarboxylic acids of the formula I, wherein sucrosemonocarboxylic acids of the formula II

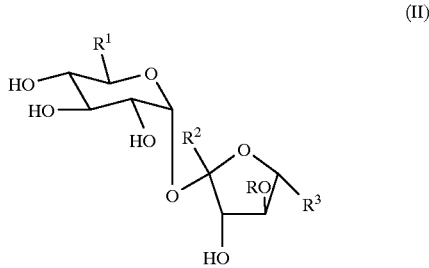

(II)

or a mixture thereof are reacted in pyridine with carboxylic anhydride or carbonyl chloride whose carboxylic acid residue is —CO—R', where R', $R^1$, $R^2$, $R^3$ and n have the abovementioned meaning. In a preferred embodiment, the invention relates to a process for the preparation of the acylated sucrosemonocarboxylic acids, in which 0.003 to 0.03 mol of sucrosemonocarboxylic acids are reacted, either as single component or as mixture thereof, in pyridine with 0.003 to 0.5 mol of carboxylic anhydrides or carbonyl chlorides, which can be employed pure or dissolved in chloroform, with or without catalyst.

The invention also relates, in a further embodiment, to a process for the preparation of the compounds according to the invention, in which the reaction of the sucrosemonocarboxylic acids of the formula II or mixtures thereof takes place without solvent, in particular in the presence of potassium carbonate and potassium stearate, with carboxylic esters, preferably methyl or ethyl esters, preferably fatty acid esters thereof. In this embodiment of the invention it is particularly preferred to employ 0.003 mol to 0.02 mol of fatty acid ester and 0.003 mol to 0.03 mol of the sucrosemonocarboxylic acid or mixture thereof.

The ratio of hydrophilicity to hydrophobicity, which is particularly important for the suitability of the compounds according to the invention as surface-active substances, is adjusted via the alkyl substituents and the degree of acylation. The degree of acylation or substitution of the compound according to the invention indicates how many of the hydroxyl groups present are acylated. The degree of acylation can be adjusted via the molar ratio of the aliphatic carboxylic acid derivative to the sucrosemonocarboxylic acid and is stated as an average. The sucrosemonocarboxylic acids used according to the invention have seven free hydroxyl groups, the eight hydroxyl group being in carboxylate form. The degree of acylation can accordingly be between 1 and 7. It is preferred according to the invention for the degree of acylation to be $\leq 3$, particularly preferably $\leq 2$.

In a particularly preferred embodiment of the invention, the carboxylic acid residue in the compounds preferably employed as anhydrides or acid chlorides for preparing the acylated sucrosemonocarboxylic acids is a caproic, caprylic, capric, lauric, myristic, palmitic or stearic acid residue. The acylation takes place, when anhydrides or chlorides are used, in particular at temperatures between 0° C. and 100° C., preferably between 20° C. and 50° C.

In another preferred embodiment of the invention, the ethyl or methyl esters employed for the solvent-free preparation of the acylated sucrosemonocarboxylic acids are, in particular, esters of fatty acids, preferably of capric acid, lauric acid, myristic acid, palmitic acid and stearic acid. The acylation takes place in the solvent-free preparation of the compound according to the invention in particular between 100° C. and 200° C., preferably between 120° C. and 180° C.

The invention also relates to the abovementioned processes in which a catalyst is additionally used. Particularly used as catalyst is 4-(dimethylamino)pyridine or potassium carbonate with potassium stearate.

The compounds obtained by the process according to the invention are analyzed by spectroscopic methods such as IR, $^1$H- and $^{13}$C-NMR. The relevant characteristic data are as follows:

IR spectrum: the carbon-hydrogen stretching vibration of the substituent is located at 2900 $cm^{-1}$, the carbonyl stretching vibration of the ester is in the range 1720 to 1750 $cm^{-1}$, the carboxylate stretching vibration is in the range 1660 to 1710 $cm^{-1}$, and the carbon-oxygen stretching vibration is in the range 1050 to 1250 $cm^{-1}$;

$^1$H-NMR spectrum: the substituent signals are located at 2.3 ppm and in the range 0.9 to 1.6 ppm, and the carbohydrate signals are in the range 5.2 to 5.7 ppm and in the range 3.4 to 4.6 ppm;

$^{13}$C-NMR: the signals of the carbonyl carbon atoms are located in the range 175 to 180 ppm, the aliphatic substituent signals in the range 14 to 33 ppm, the sucrose framework in the ranges 103 to 105 ppm, 92 to 94 ppm and 61 to 83 ppm.

The degree of acylation of the compounds according to the invention is established using the proton ratio by integration of the $^1$H-NMR signal.

The following examples illustrate the invention:

EXAMPLE 1

Acylation of 1-O-(β-D-fructofuranuronyl)-α-D-glucopyranoside ($C_6$-sucrosemonocarboxylic acid) with caproyl chloride without catalyst 10 g (0.03 mol) of $C_6$-sucrosemonocarboxylic acid are dissolved in 500 ml of pyridine in a temperature-controllable reactor with stirrer. At 0° C., 8.2 ml (0.06 mol) of caproyl chloride dissolved in 8 ml of chloroform are added dropwise. After 24 h at 25° C., 500 ml of water are added to the reaction mixture at 0° C., and the mixture is concentrated under vacuum (15 hPa). The residue is taken up in 100 ml of water, and the solution is extracted with ethyl acetate (4×50 ml) and lyophilized. The product is obtained as colorless solid in a yield of 60% by weight (degree of acylation 1). The surface tension of a 0.8% by weight aqueous solution is 54.3 mN/m.

EXAMPLE 2
Acylation of 2-keto-6-O-($\alpha$-D-glucopyranosyl)-$\beta$-D-glucofuranonic acid ($C_1$-sucrosemonocarboxylic acid) with caproyl chloride without catalyst 5 g (0.014 mol) of $C_1$-sucrosemonocarboxylic acid are dissolved in 250 ml of pyridine in a temperature-controllable reactor with stirrer. At 0° C., 4.1 ml (0.03 mol) of caproyl chloride dissolved in 4 ml of chloroform are added dropwise. After 24 h at 25° C., 250 ml of water are added to the reaction mixture at 0° C., and the mixture is concentrated under vacuum (15 hPa). The residue is taken up in 75 ml of water, and the solution is extracted with ethyl acetate (4×30 ml) and lyophilized. The product is obtained as colorless solid in a yield of 58% by weight (degree of acylation 1). The surface tension of a 0.8% by weight aqueous solution is 54.1 mN/m.

EXAMPLE 3
Acylation of 1-O-($\beta$-D-fructofuranosyl)-$\alpha$-D-glucopyranuronide ($C_{6'}$-sucrosemonocarboxylic acid) with capryloyl chloride without catalyst 10 g (0.028 mol) of $C_{6'}$-sucrosemonocarboxylic acids are dissolved in 500 ml of pyridine in a temperature-controllable reactor with stirrer. At 0° C., 8.6 ml (0.06 mol) of capryloyl chloride are added dropwise. After 48 h at 25° C., 500 ml of water are added to the reaction mixture at 0° C., and the mixture is concentrated under vacuum (15 hPa). The residue is taken up in 100 ml of water, and the solution is extracted with ethyl acetate (4×50 ml) and lyophilized. The product is obtained as colorless solid in a yield of 55% by weight (degree of acylation 1). The surface tension of a 1.4% by weight aqueous solution is 29.5 mN/m.

EXAMPLE 4
Acylation of sucrosemonocarboxylic acids with capryloyl chloride without catalyst 10 g (0.03 mol) of sucrosemonocarboxylic acids ($C_6$, $C_1$ and $C_{6'}$ acids as mixture, ratio 45:10:45 by weight) are dissolved in 500 ml of pyridine in a temperature-controllable reactor with stirrer. At 0° C., 8.6 ml (0.06 mol) of capryloyl chloride are added dropwise. After 48 h at 25° C., 500 ml of water are added to the reaction mixture at 0° C., and the mixture is concentrated under vacuum (15 hPa). The residue is taken up in 100 ml of water, and the solution is extracted with ethyl acetate (4×50 ml) and lyophilized. The product is obtained as colorless solid in a yield of 55% by weight (degree of acylation 1). The surface tension of a 1.6% by weight aqueous solution is 29.2 mN/m.

EXAMPLE 5
Catalytic acylation of sucrosemonocarboxylic acids with capric anhydride 5 g (0.014 mol) of sucrosemonocarboxylic acids ($C_6$, $C_1$ and $C_{6'}$ acids as mixture, ratio 40:10:50 by weight) are dissolved in 200 ml of pyridine in a temperature-controllable reactor with stirrer, and 0.9 g (0.007 mol) of 4-(dimethylamino)pryridine is added. At 0° C., 18.4 ml (0.05 mol) of capric anhydride are added dropwise. After 48 h at 40° C., 200 ml of water are added to the reaction mixture at 0° C., and the mixture is concentrated under vacuum (15 hPa). The residue is taken up in 100 ml of water, and the solution is extracted with ethyl acetate (5×50 ml) and lyophilized. The product is obtained as slightly colored solid in a yield of 55% by weight (degree of acylation 1.5). The surface tension of a 0.7% by weight aqueous solution is 24.2 mN/m.

EXAMPLE 6
Catalytic acylation of sucrosemonocarboxylic acids with lauroyl chloride 5 g (0.014 mol) of sucrosemonocarboxylic acids ($C_6$, $C_1$ and $C_{6'}$ acids as mixture, ratio 50:5:45 by weight) are dissolved in 200 ml of pyridine in a temperature-controllable reactor with stirrer, and 1.5 g (0.012 mol) of 4-(dimethylamino)pryridine is added. At 0° C., 6.6 ml (0.03 mol) of lauroyl chloride dissolved in 7 ml of chloroform are added dropwise. After 48 h at 25° C., 200 ml of water are added to the reaction mixture at 0° C., and the mixture is concentrated under vacuum (15 hPa). The residue is taken up in 100 ml of water, and the solution is extracted with ethyl acetate (5×50 ml) and lyophilized. The product is obtained as slightly colored solid in a yield of 55% by weight (degree of acylation 1). The surface tension of a 1% by weight aqueous solution is 28.9 mN/m.

EXAMPLE 7
Catalytic acylation of sucrosemonocarboxylic acids with lauroyl chloride 5 g (0.014 mol) of sucrosemonocarboxylic acids ($C_6$, $C_1$ and $C_{6'}$ acids as mixture, ratio 50:5:45 by weight) are dissolved in 200 ml of pyridine in a temperature-controllable reactor with stirrer, and 0.9 g (0.007 mol) of 4-(dimethylamino)pryridine is added. At 0° C., 23.8 ml (0.1 mol) of lauroyl chloride dissolved in 25 ml of chloroform are added dropwise. After 48 h at 25° C., 200 ml of water are added to the reaction mixture at 0° C., and the mixture is concentrated under vacuum (15 hPa). The residue is taken up in 100 ml of ethyl acetate, and the solution is extracted with water (4×25 ml), dried and concentrated. The product is obtained as a slightly colored solid in a yield of 70% by weight (degree of acylation 5).

EXAMPLE 8
Solvent-free acylation of sucrosemonocarboxylic acids with methyl palmitate A mixture of 10 g (0.028 mol) of sucrosemonocarboxylic acids ($C_6$, $C_1$ and $C_{6'}$ acids as mixture, ratio 50:5:45 by weight), 5.4 g (0.022 mol) of methyl palmitate, 0.81 g (0.002 mol) of potassium stearate and 0.15 g (0.001 mol) of potassium carbonate is extruded by a twin-screw extruder into a reactor and heated at 160° C. under 100 mbar for 60 min. The resulting crude product is suspended in 100 ml. of water and filtered, and the filtrate is extracted with diethyl ether (3×50 ml) and subsequently freeze-dried. The lyophilisate is extracted with boiling butanol (300 ml) in a Soxhlet apparatus for 8 h. The product can be obtained from the concentrated extract phase as slightly colored solid in a yield of 45% by weight (degree of acylation 1). The surface tension of a 1% by weight aqueous solution is 35 mN/m.

EXAMPLE 9
Determination of the Surface Tension

The compounds according to the invention, especially those with a degree of acylation $\leq 3$, have surface-active properties. Table 1 illustrates how the compounds according to the invention reduce the surface tension of water. The surface tension $\sigma$ of aqueous solutions of the acylated sucrosemonocarboxylic acids according to the invention was measured by the Wilhelmy method at 25° C. The compound according to the invention is indicated in Table 1 in short form as salt of the fatty acid used for the acylation (DS means degree of substitution, the % by weight figure relates to the concentration of the solution).

TABLE 1

| Surface tension | |
| --- | --- |
| Sample | σ (mN/m) |
| Caproate (DS ≈ 1; 0.8%) | 54.3 |
| Caprylate (DS ≈ 1; 1.6%) | 29.2 |
| Caprate (DS 1.5; 0.7%) | 24.2 |
| Laurate (DS ≈ 1; 1%) | 28.9 |

The reduction in the surface tension of water brought about by the compounds according to the invention makes these compounds particularly suitable for use in detergents, rinsing agents, and cleaners, and as emulsifiers, for example in the foodstuffs, sweeteners, and pharmaceuticals sectors.

EXAMPLE 10
Solubilization of Sudan Red B in Water Using acylated sucrosemonocarboxylic acids Solutions of acylated sucrosemonocarboxylic acids of various concentrations (0.06 g, 0.12 g and 0.24 g in 20 ml of water) were each mixed with 0.01 g of Sudan Red B. The dye was dispersed ultrasonically. The suspension was subsequently centrifuged at 7000 rpm for 60 min and membrane-filtered (regenerated cellulose, 0.2 μm). The extinction of the supernatant clear solution was measured by photometry at a wavelength of 516 nm (cuvette length 1 cm). A solution of Sudan Red B in water (0.01 g in 20 ml) which had been pretreated like the ester solution was used as zero sample. Table 2 indicates by way of example the results for the caprylate of the sucrosemonocarboxylic acids (degree of acylation 1).

TABLE 2

| Solubilization | |
| --- | --- |
| Concentration of the caprylate ox. sucrose (% by weight), degree of acylation 1 | Extinction |
| 0 | 0.0096 |
| 0.6 | 0.0654 |
| 1.2 | 0.1513 |

The table shows that the compounds according to the invention have excellent solubilizing properties. The compounds are accordingly suitable, for example, for detergents, rinsing agents, and cleaners.

EXAMPLE 11
Preparation of a Shampoo

To prepare 100 g of a shampoo, 10 g of the compounds according to the invention (laurate of $C_6$-, $C_1$- and $C_{6'}$-sucrosemonocarboxylic acids), 15 g of Tego betaine, 2 g of NaCl, 0.2 g of preservative and 0.5 g of perfume oil are mixed and made up to 100 g with water. A highly effective shampoo which is compatible with skin and hair is obtained.

EXAMPLE 12
Preparation of a Scouring Composition

To prepare 100 g of a scouring composition, 4 g of the compounds according to the invention (caprate of $C_6$-, $C_1$- and $C_{6'}$-sucrosemonocarboxylic acids) 2 g of octadecyl polyethylene glycol ether, 5 g of pentasodium triphosphate, 1 g of fragrance are mixed and made up to 100 g with quartz powder.

EXAMPLE 13

Preparation of a Detergent

To prepare 100 g of a detergent, 20 g of the compounds according to the invention (laurate of $C_6$-, $C_1$- and $C_{6'}$-sucrosemonocarboxylic acids), 20 g of complexing agent (zeolite), 0.5 g of proteases, 4 g of sodium citrate, 10 g of ethanol, optionally perfume and dye, are mixed and made up to 100 g with water.

EXAMPLE 14

Preparation of a Bath Additive

To prepare 100 g of a bath additive, 25 g of the compounds according to the invention (laurate of $C_6$-, $C_1$-and $C_{6'}$-sucrosemonocarboxylic acids), 5 g of coconut fatty acid ethanolamide, 6 g of almond oil, 1 g of sodium chloride, 0.4 g of preservative, 1 g of hexadecanol, 2 g of perfume are mixed and made up to 100 g with water.

We claim:

1. An acylated sucrosemonocarboxylic acid of the formula I

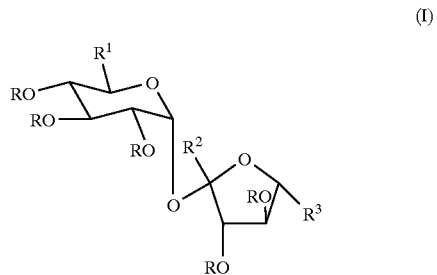

(I)

in which one of $R^1$, $R^2$, or $R^3$ is COOH and the other two of $R^1$, $R^2$, or $R^3$ are $CH_2OH$, and R is H or CO—R', at least one R being CO—R', where R' is $(CH_2)_n$—$CH_3$ with n=4–16.

2. Acylated sucrosemonocarboxylic acid according to claim 1, characterized in that when more than one R is CO—R', the R' radicals are different.

3. Acylated sucrosemonocarboxylic acid according to claim 1, characterized in that —CO—R' is a caproic acid, caprylic acid, capric acid, lauric acid, myristic acid, palmitic acid, or stearic acid residue.

4. Acylated sucrosemonocarboxylic acid according to claim 1, characterized in that the degree of acylation thereof is ≦2.

5. An aqueous solution containing at least one acylated sucrosemonocarboxylic acid according to claim 1.

6. Powder containing at least one acylated sucrosemonocarboxylic acid according to claim 1.

7. A process for the preparation of an acylated sucrosemonocarboxylic acid according to claim 1, characterized in that a sucrosemonocarboxylic acid of the formula II

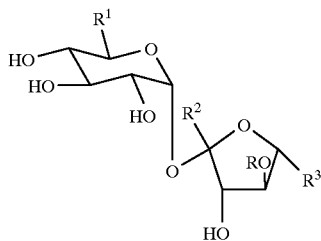

is reacted in pyridine with carboxylic anhydride or carbonyl chloride whose carboxylic acid residue is —CO—R', wherein one of $R^1$, $R^2$, or $R^3$ is COOH and the other two of $R^1$, $R^2$, or $R^3$ are $CH_2OH$, and R is H or CO—R', at least one R being CO—R', where R' is $(CH_2)_n$—$CH_3$ with n=4–16.

8. The process according to claim 7, characterized in that the carboxylic acid residue —CO—R' is a caproic acid, caprylic acid, capric acid, lauric acid, myristic acid, palmitic acid or stearic acid residue.

9. The process according to claim 7, characterized in that the reaction takes place at 0° C. to 100° C.

10. A process for the preparation of an acylated sucrosemonocarboxylic acid according to claim 1, characterized in that a sucrosemonocarboxylic acid of the formula II

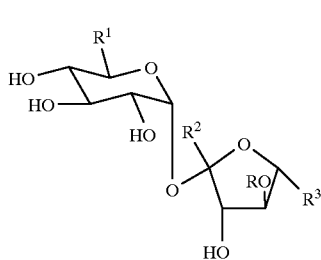

undergoes solvent-free catalytic reaction with a carboxylic ester whose carboxylic acid residue is —CO—R', wherein one of $R^1$, $R^2$ or $R^3$ is COOH and the other two of $R^1$, $R^2$, or $R^3$ are $CH_2OH$, and R is H or CO—R', at least one R being CO—R', where R' is $(CH_2)_n$—$CH_3$ with n=4–16.

11. The process according to claim 10, characterized in that the carboxylic esters are methyl or ethyl esters of capric acid, lauric acid, myristic acid, palmitic acid or stearic acid.

12. The process according to claim 10, characterized in that the reaction takes place at 100° C. to 200° C.

13. The process according to claim 7, characterized in that a catalyst is used.

14. The process according to claim 13, characterized in that the catalyst is 4-(dimethylamino)pyridine or potassium carbonate with potassium stearate.

15. Detergent containing at least one acylated sucrosemonocarboxylic acid according to claim 1.

16. The process according to claim 9, wherein the reaction takes place at 20° C. to 50° C.

17. The process according to claim 12, wherein the reaction takes place at 120° C. to 180° C.

18. A method for imparting surface-active activity to a detergent, rising agent, or cleaner comprising adding to said detergent, rising agent or cleaner an effective amount of an acylated sucrosemonocarboxylic acid according to claim 1.

* * * * *